US011700997B2

(12) United States Patent
Viering et al.

(10) Patent No.: US 11,700,997 B2
(45) Date of Patent: Jul. 18, 2023

(54) IMAGE PROCESSING SYSTEMS AND METHODS OF USING THE SAME

(71) Applicant: Boston Scientific Scimed, Inc., Maple Grove, MN (US)

(72) Inventors: Kirsten Viering, Newton, MA (US); George Wilfred Duval, Sudbury, MA (US); Louis J. Barbato, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 32 days.

(21) Appl. No.: 17/458,774

(22) Filed: Aug. 27, 2021

(65) Prior Publication Data
US 2022/0070416 A1 Mar. 3, 2022

Related U.S. Application Data

(60) Provisional application No. 63/073,126, filed on Sep. 1, 2020.

(51) Int. Cl.
*A61B 1/05* (2006.01)
*G06T 7/10* (2017.01)
(Continued)

(52) U.S. Cl.
CPC .............. *A61B 1/05* (2013.01); *A61B 1/0638* (2013.01); *G06F 18/213* (2023.01); *G06T 3/40* (2013.01);
(Continued)

(58) Field of Classification Search
CPC .. H04N 23/84; G06T 7/10; G06T 7/20; G06T 3/40; G06T 2207/30004; G06T 11/001;
(Continued)

(56) References Cited

U.S. PATENT DOCUMENTS

2012/0184841 A1\* 7/2012 Nielsen ............... A61N 5/1071
600/411
2014/0155717 A1 6/2014 Saito
(Continued)

FOREIGN PATENT DOCUMENTS

WO 2014160510 A2 10/2014

OTHER PUBLICATIONS

Danail Stoyanov et al: "Robust registration of multispectral images of the cortical surface in neurosurgery", Biomedical Imaging (ISBI), 2012 9th IEEE International Symposium on, IEEE, May 2, 2012 (May 2, 2012), pp. 1643-1646, XP032199350, DOI: 10.1109/ISBI. 2012.6235892 ISBN: 978-1-4577-1857-1 abstract; figure 2 sections: 2.1. Optical imaging system; 2.2. Preprocessing and initial correspondence; 2.3. Surface model; 2.4 Energy function.
(Continued)

*Primary Examiner* — Allen C Wong
(74) *Attorney, Agent, or Firm* — Bookoff McAndrews, PLLC

(57) ABSTRACT

A method of generating a color image using a monochromatic image sensor. The method includes sequentially illuminating a surface in a plurality of colors, one color at a time. The monochromatic image sensor captures a plurality of image frames of the surface based on the plurality of colors. The plurality of image frames are identified, and at least one feature in the target of the plurality of image frames is highlighted. Color intensities of the plurality of image frames are normalized. A color intensity map of the target for each of the plurality of image frames is generated. A correlation score is determined by comparing each color intensity map of the plurality of image frames. The color image is generated based on the correlation score.

20 Claims, 5 Drawing Sheets

(51) Int. Cl.
  *G06V 20/00* (2022.01)
  *A61B 1/06* (2006.01)
  *G06T 3/40* (2006.01)
  *G06T 7/20* (2017.01)
  *G06T 11/00* (2006.01)
  *G06F 18/213* (2023.01)
  *H04N 23/84* (2023.01)

(52) U.S. Cl.
  CPC .............. *G06T 7/10* (2017.01); *G06T 7/20* (2013.01); *G06T 11/001* (2013.01); *G06V 20/00* (2022.01); *H04N 23/84* (2023.01); *G06T 2207/30004* (2013.01); *G06V 2201/03* (2022.01)

(58) Field of Classification Search
  CPC .. G06V 20/00; G06V 2201/03; G06F 18/213; A61B 1/05; A61B 1/0638
  USPC .......................................................... 348/71
  See application file for complete search history.

(56) References Cited

U.S. PATENT DOCUMENTS

2021/0267443 A1\* 9/2021 Baumann ................ H04N 7/183
2022/0187584 A1\* 6/2022 Ha ........................ G02B 21/367

OTHER PUBLICATIONS

International Search Report issued in International Application No. PCT/US2021/047859 dated Dec. 10, 2021 (15 pages).

\* cited by examiner

IMAGE PROCESSING SYSTEMS AND METHODS OF USING THE SAME

CROSS-REFERENCE TO RELATED APPLICATIONS

This application claims the benefit of priority from U.S. Provisional Application No. 63/073,126, filed on Sep. 1, 2020, which is incorporated by reference herein in its entirety.

TECHNICAL FIELD

Various aspects of the disclosure relate generally to image processing systems, devices, and related methods. Examples of the disclosure relate to systems, devices, and related methods for estimating motion and colorizing images captured by monochromatic sensors, among other aspects.

BACKGROUND

Technological developments have given users of medical systems, devices, and methods, the ability to conduct increasingly complex medical procedures on various patients. However, in the field of minimally invasive surgeries, accurately visualizing target treatment sites within a patient, for example, tumors or lesions located in a gastrointestinal tract of the patient, is a known challenge. Although the treatment site images captured by monochromatic sensors may provide high quality contrast definition as well as spectral flexibility, limitations in imaging methods and devices for colorizing the images of target treatment sites may overburden the image processors, cause image processing delays, and/or limit its effectiveness.

SUMMARY

Aspects of the disclosure relate to, among other things, systems, devices, and methods for providing an image processing system and target extraction logic, intensity normalization logic, and intensity correlation logic, among other aspects. Each of the aspects disclosed herein may include one or more of the features described in connection with any of the other disclosed aspects.

According to one aspect, a method is provided for generating a color image using a monochromatic image sensor. The method includes sequentially illuminating a surface in a plurality of colors, one color at a time. The monochromatic image sensor captures a plurality of image frames of the surface based on the plurality of colors. The plurality of image frames are identified, and at least one feature in the target of the plurality of image frames is highlighted. Color intensities of the plurality of image frames are normalized. A color intensity map of the target for each of the plurality of image frames is generated. A correlation score is determined by comparing each color intensity map of the plurality of image frames. The color image is generated based on the correlation score.

Any of the methods described herein may include any of the following steps. The plurality of image frames includes at least a first image frame in a first color and a second image frame in a second color. The color intensities of the plurality of image frames is normalized by illuminating the surface with a first color of the plurality of colors. An intensity of the illuminated first color is determined. A normalization value is assigned to the intensity of the first color. The surface is illuminated with a second color of the plurality of colors. An intensity of the illuminated second color is determined. A normalized intensity value of the second color is generated based on the normalization value. The plurality of colors comprises at least one of red, green, or blue. The at least one feature in the target is highlighted by applying an edge filter to extract at least one edge in the at least one feature. The color intensity maps comprise a plurality of pixels, and each of the plurality of pixels has a color intensity value. The target in each of the plurality of image frames is compared based on the color intensity maps of the plurality of image frames. A matching pixel of the target between a first color intensity map and a second color intensity map is determined when the correlation score is above a predetermined threshold value. The plurality of frames is downsampled. The correlation score is determined after downsampling the plurality of frames. The plurality of frames is downsampled by a factor of two at least twice. Peak intensity clusters in the color intensity maps are determined. The motion of the target is estimated by comparing the peak intensity clusters in a first color intensity map and a second color intensity map. The correlation score is determined in less than 150 milliseconds. The surface comprises a tissue of a gastrointestinal tract.

According to one aspect, a medical device includes a shaft, a monochromatic image sensor coupled to a distal end of the shaft, and at least one illumination device coupled to the distal end of the shaft. The at least one illumination device is configured to emit a plurality of colors, one color at a time. The medical device further includes one or more computer readable media storing instructions for performing an image processing using the monochromatic image sensor and one or more processors configured to execute the instructions to perform the image processing. The one or more processors are configured to sequentially illuminate a surface in a plurality of colors. The monochromatic image sensor captures a plurality of image frames of the surface based on the plurality of colors. The one or more processors identify a target in the plurality of image frames. The one or more processors highlight at least one feature in the target of the plurality of image frames. The one or more processors normalize color intensities of the plurality of image frames. The one or more processors generate a color intensity map of the target for each of the plurality of image frames. The one or more processors determine a correlation score by comparing each color intensity map of the plurality of image frames. The one or more processors generate the color image based on the correlation score.

Any of the medical devices described herein may include any of the following features. The at least one illumination device is configured to selectively emit at least one of red, blue, and green colors. The one or more processors normalize the color intensities by illuminating the surface with a first color of the plurality of colors, determining an intensity of the illuminated first color, and assigning a normalization value to the intensity of the first color. The one or more processors normalize the color intensities of the plurality of image frames by illuminating the surface with a second color of the plurality of colors, determining an intensity of the illuminated second color, and generating a normalized intensity value of the second color based on the normalization value.

According to one aspect, a non-transitory computer-readable medium stores instructions for performing image processing using a monochromatic image sensor. The instructions, when executed by one or more processors, causes one or more processors to perform operations. The one or more processors sequentially illuminate a surface in a plurality of colors, one color at a time. The monochromatic images sensor captures a plurality of image frames of the surface based on the plurality of colors. The one or more processors identify a target in the plurality of image frames. The one or more processors highlight at least one feature in the target of the plurality of image frames. The one or more processors normalize color intensities of the plurality of image frames. The one or more processors generate a color intensity map of the target for each of the plurality of image frames. The one or more processors determine a correlation score by comparing each color intensity map of the plurality of image frames. The one or more processors generate the color image based on the correlation score.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1:
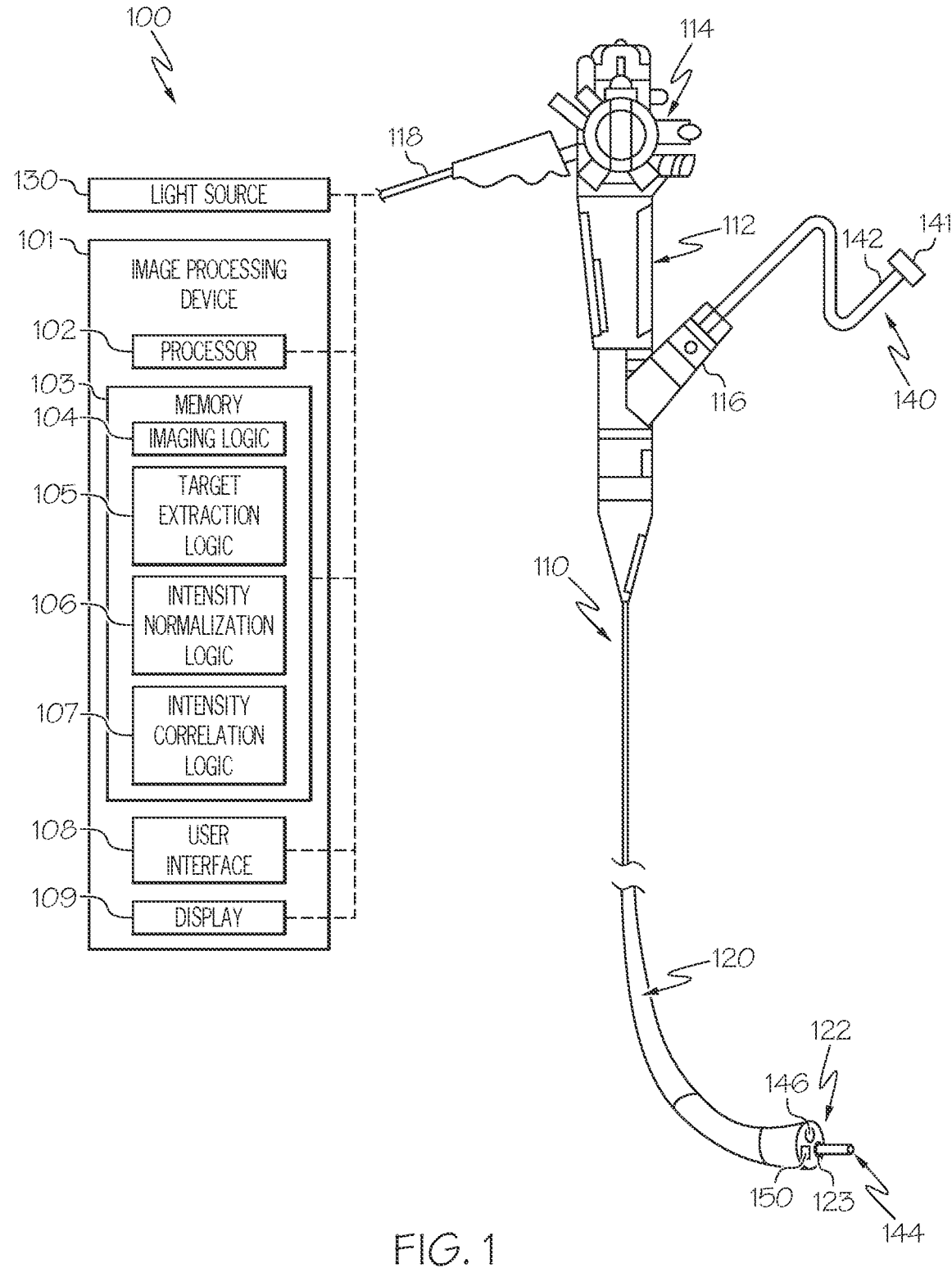
FIG. 1 is a schematic view of an exemplary medical system, according to aspects of this disclosure.

Examples of the disclosure include systems, devices, and methods for enhancing images of one or more target treatment sites within a subject (e.g., patient) by capturing images using one or more monochromatic sensors and identifying one or more features (e.g., blood vessels, other features of the vascular system, tissue features, abnormalities, etc.) of the target site to accurately colorize the captured images. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may be used to identify target sites within a subject by generating processed images based on multiple image frames of multimodal spectrum captured by one or more monochromatic image sensors of a medical system. In some embodiments, a medical device may include an image processing device including a processor and a memory storing one or more executable instructions and algorithms for detecting motion of target site features. Further, the processor and the memory may generate relative pixel blocks for colorizing images based on the detected motion of the target site features in the multiple image frames of multimodal spectrum captured by the one or more monochromatic image sensors. In embodiments, the memory may include programmable and executable instructions in accordance with an imaging logic, a target extraction logic, an intensity normalization logic, and an intensity correlation logic. Further, the image processing device may include a user interface operable to receive a user input thereon. The processed image produced by the image processing device of the medical device may include a colorized resolution frame of pixel values that may be outputted to a display device.

Examples of the disclosure may relate to systems, devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices. Reference will now be made in detail to examples of the disclosure described above and illustrated in the accompanying drawings. Wherever possible, the same reference numbers will be used throughout the drawings to refer to the same or like parts.

FIG. 1 shows a schematic depiction of an exemplary medical system 100 in accordance with an example of this disclosure. The medical system 100 may include one or more light sources 130, an image processing device 101, a medical instrument 110, and a medical device 140. The image processing device 101 may be communicatively coupled to the medical instrument 110 by, for example, a wired connection, a wireless connection, and the like. In examples, the image processing device 101 is a computer system incorporating a plurality of hardware components that allow the image processing device 101 to receive data (e.g., image sensor data), process information (e.g., intensity, motion, or spectral data and the like), and/or generate a processed image for outputting to a user of the medical system 100. Illustrative hardware components of the image processing device 101 may include at least one processor 102, at least one memory 103, at least one user interface 108, and at least one display 109.

The processor 102 of the image processing device 101 may include any computing device capable of executing machine-readable instructions, which may be stored on a non-transitory computer-readable medium, for example, the memory 103 of the image processing device 101. By way of example, the processor 102 may include a controller, an integrated circuit, a microchip, a computer, and/or any other computer processing unit operable to perform calculations and logic operations required to execute a program. As described in greater detail herein, the processor 102 is configured to perform one or more operations in accordance with the instructions stored on the memory 103.

Still referring to FIG. 1, the memory 103 of the image processing device 101 may include a non-transitory computer readable medium that stores machine-readable instructions thereon, for example, an imaging logic 104, a target extraction logic 105, an intensity normalization logic 106, and an intensity correlation logic 107. The imaging logic 104 may include executable instructions or algorithms that allow the medical system 100 to capture digital images (e.g., raw digital images) by activating one or more components of the medical instrument 110, for example, one or more image sensors 150 and one or more light sources 130. The one or more image sensors 150 may include, for example, one or more monochromatic image sensors. The one or more light sources 130 may be configured to emit white light, color light (e.g., red, blue, and green), ultraviolet light, near-infrared (NIR) light, and/or various other wavelengths within or beyond a visible spectrum. The one or more light sources 130 may be one or more light-emitting diodes (hereinafter LEDs). Further, the image sensor 150 (or one or more image sensors) of the medical instrument 110 may be communicatively coupled to the image processing device 101 of the medical system 100, for example, via a wired connection, a wireless connection, and/or the like. The image sensor 150 of the medical instrument 110 may be configured and operable to capture a raw image (e.g., a digital image) of a surrounding environment of the tip 122 of the shaft 120.

In one embodiment, the image sensor 150 may include a photosensor array (not shown) that may be configured and operable to convert a light beam received by the photosensor array into an electrical current. For example, the electrical current may be generated by the photosensor array arranged on the image sensor 150 when photons from the received light are absorbed by a plurality of photosites (not shown) arranged on the photosensor array. Further, each of the plurality of photosites may be operable to receive, capture, and absorb different wavelengths of the incoming light at a location of the photosites along a surface of the photosensor array. Accordingly, the plurality of photosites may capture the incoming light and may generate an electrical signal which is quantified and stored as a numerical value in a resulting processed image file. It should be appreciated that the photosensor array may include various suitable shapes, sizes, and/or configurations.

Still referring to FIG. 1, the target extraction logic 105 may include executable instructions or algorithms that allow the medical system 100 to, for example, identify features in target sites of a subject. The intensity normalization logic 106 may include executable instruction or algorithms that allow the medical system 100 to, for example, normalize image data obtained from a plurality of frames of multi-modal spectrum. The intensity correlation logic 107 may include executable instruction or algorithms that allow the medical system 100 to, for example, generate pixel to pixel intensity maps and identify a best fit match between the generated intensity maps to obtain relative pixel blocks utilized for colorizing the image captured by monochromatic image sensors.

In some embodiments, the imaging logic 104, the target extraction logic 105, the intensity normalization logic 106, and/or the spatial correlation logic 107 may include executable instructions and algorithms that allow the medical system 100 to execute periodic image processing of a target site automatically without requiring user input. In other embodiments, the image processing device 101 may be configured to receive user inputs to initiate image processing of a target site, for example, from a user interface 108 of the image processing device 101. It should be appreciated that, in some embodiments, the user interface 108 may be a device integral with the image processing device 101, and in other embodiments, the user interface 108 may be a remote device in communication (e.g., wireless, wired, etc.) with the image processing device 101, including switches, buttons, or other inputs on the medical instrument 110.

It should be understood that various programming algorithms and data that support an operation of the medical system 100 may reside in whole or in part in the memory 103. The memory 103 may include any type of computer readable medium suitable for storing data and algorithms, such as, for example, random access memory (RAM), read only memory (ROM), a flash memory, a hard drive, and/or any device capable of storing machine-readable instructions. The memory 103 may include one or more data sets, including, but not limited to, image data from one or more components of the medical system 100 (e.g., the medical instrument 110, the medical device 140, etc.).

Still referring to FIG. 1, the medical instrument 110 may be configured to facilitate positioning of one or more components of the medical system 100 relative to a subject (e.g., a patient), such as, for example, the medical device 140. In some embodiments, the medical instrument 110 may be any type of endoscope, duodenoscope, gastroscope, colonoscope, ureteroscope, bronchoscope, catheter, or other delivery system, and may include a handle 112, an actuation mechanism 114, at least one port 116, and a shaft 120. The handle 112 of the medical instrument 110 may have one or more lumens (not shown) that communicate with a lumen(s) of one or more other components of the medical system 100. The handle 112 further includes the at least one port 116 that opens into the one or more lumens of the handle 112. As described in further detail herein, the at least one port 116 is sized and shaped to receive one or more instruments therethrough, such as, for example, the medical device 140 of the medical system 100.

The shaft 120 of the medical instrument 110 may include a tube that is sufficiently flexible such that the shaft 120 is configured to selectively bend, rotate, and/or twist when being inserted into and/or through a subject's tortuous anatomy to a target treatment site. The shaft 120 may have one or more lumens (not shown) extending therethrough that include, for example, a working lumen for receiving instruments (e.g., the medical device 140). In other examples, the shaft 120 may include additional lumens such as a control wire lumen for receiving one or more control wires for actuating one or more distal parts/tools (e.g., an articulation joint, an elevator, etc.), a fluid lumen for delivering a fluid, an illumination lumen for receiving at least a portion of an illumination assembly (not shown), and/or an imaging lumen for receiving at least a portion of an imaging assembly (not shown).

Still referring to FIG. 1, the medical instrument 110 may further include a tip 122 at a distal end of the shaft 120. In some embodiments, the tip 122 may be attached to the distal end of the shaft 120, while in other embodiments the tip 122 may be integral with the shaft 120. For example, the tip 122 may include a cap configured to receive the distal end of the shaft 120 therein. The tip 122 may include one or more openings that are in communication with the one or more lumens of the shaft 120. For example, the tip 122 may include a working opening 123 through which the medical device 140 may exit from a working lumen of the shaft 120. It should be appreciated that other one or more openings at the tip 122 of the shaft 120 are not shown. The actuation mechanism 114 of the medical instrument 110 is positioned on the handle 112 and may include one or more knobs, buttons, levers, switches, and/or other suitable actuators.

The actuation mechanism 114 is configured to control at least a deflection of the shaft 120 (e.g., through actuation of a control wire).

The medical device 140 of the medical system 100 may include a catheter having a longitudinal body 142 between a proximal end 141 of the medical device 140 and a distal end 144 of the medical device 140. The longitudinal body 142 of the medical device 140 may be flexible such that the medical device 140 is configured to bend, rotate, and/or twist when being inserted into a working lumen of the medical instrument 110. The medical device 140 may include a handle at the proximal end 141 of the longitudinal body 142 that may be configured to move, rotate, and/or bend the longitudinal body 142. Further, the handle at the proximal end 141 of the medical device 140 may define one or more ports (not shown) sized to receive one or more tools through the longitudinal body 142 of the medical device 140.

Still referring to FIG. 1, the medical instrument 110 may be configured to receive the medical device 140 via the at least one port 116, through the shaft 120 via a working lumen, and to the working opening 123 at the tip 122. In this instance, the medical device 140 may extend distally out of the working opening 123 and into a surrounding environment of the tip 122, such as, for example, at a target treatment site of a subject as described in further detail below. The distal end 144 of the medical device 140 may extend distally from the tip 122 in response to a translation of the longitudinal body 142 through the working lumen of the shaft 120. The medical device 140 may include one or more end effectors (not shown) at the distal end 144 of the longitudinal body 142, for performing one or more operations at a target treatment site.

In one embodiment, the medical instrument 110 may be further configured to receive the one or more light sources 130 through the shaft 120 via at least one of the lumens of the medical instrument 110 for connection to an optical fiber 146. In the example, the one or more light sources 130 are shown as a separate component from the image processing device 101 such that the light sources 130 are coupled to the medical instrument 101 separately from the image processing device (e.g., via a cable). It should be appreciated that, in other embodiments, the one or more light sources 130 may be included on the image processing device 101 such that the light sources 130 may be communicatively coupled to the medical instrument 110 with the image processing device 101.

Still referring to FIG. 1, the tip 122 of the medical instrument 110 may include the optical fiber 146 and the image sensor 150 at the tip 122. In one embodiment, the optical fiber 146 may be coupled to the one or more light sources 130 of the medical system 100, such that each of the one or more light sources 130 may transmit light through the single, optical fiber 146. Although not shown, it should be appreciated that multiple light sources 130 may be coupled to the optical fiber 146 via a fiber splitter/combiner. The optical fiber 146 of the medical instrument 110 may be configured and operable to deliver various amplitudes of light, from the one or more light sources 130, distally from the tip 122 of the shaft 120. In some embodiments, the optical fiber 146 may be configured to deliver white light, ultraviolet light, near-infrared (NIR) light, and/or various other wavelengths within or beyond a visible spectrum.

In other embodiments, the medical instrument 110 may include, although not shown, a multicolor LED assembly at the tip 122 of the shaft 120. The multicolor LED assembly may, for example, include one or more LEDs disposed in an annular array about the image sensor 150. Each of the LEDs may be configured and operable to transmit a different light wavelength and/or amplitude relative to one another. It should be understood that different illumination sources may generate different spectra (e.g., red, green, and blue colors).

In other embodiments, as further described herein, the image sensor 150 may be configured and operable to fully capture all incoming light at each individual pixel location of the image sensor 150 irrespective of a color of the incoming light.

Still referring to FIG. 1, the medical instrument 110 of the medical system 100 may be inserted within a subject's body (not shown) to position the tip 122 adjacent to a target site 201 (later shown in FIG. 2). For example, the shaft 120 may be guided through a digestive tract of a subject (e.g., patient) by inserting the tip 122 into a nose or mouth (or other suitable natural body orifice) of the subject's body and traversed through a gastrointestinal tract of the subject's body (e.g., an esophagus, a stomach, a small intestine, etc.) until reaching the target site. It should be appreciated that a length of the shaft 120 may be sufficient so that a proximal end of the medical instrument 110 (including the handle 112) is external of the subject while the tip 122 of the medical instrument 110 is internal to the subject's body. While this disclosure relates to the use of the medical system 100 in a digestive tract of a subject, it should be understood that the features of this disclosure could be used in various other locations (e.g., other organs, tissue, etc.) within a subject's body.

Figure 2:
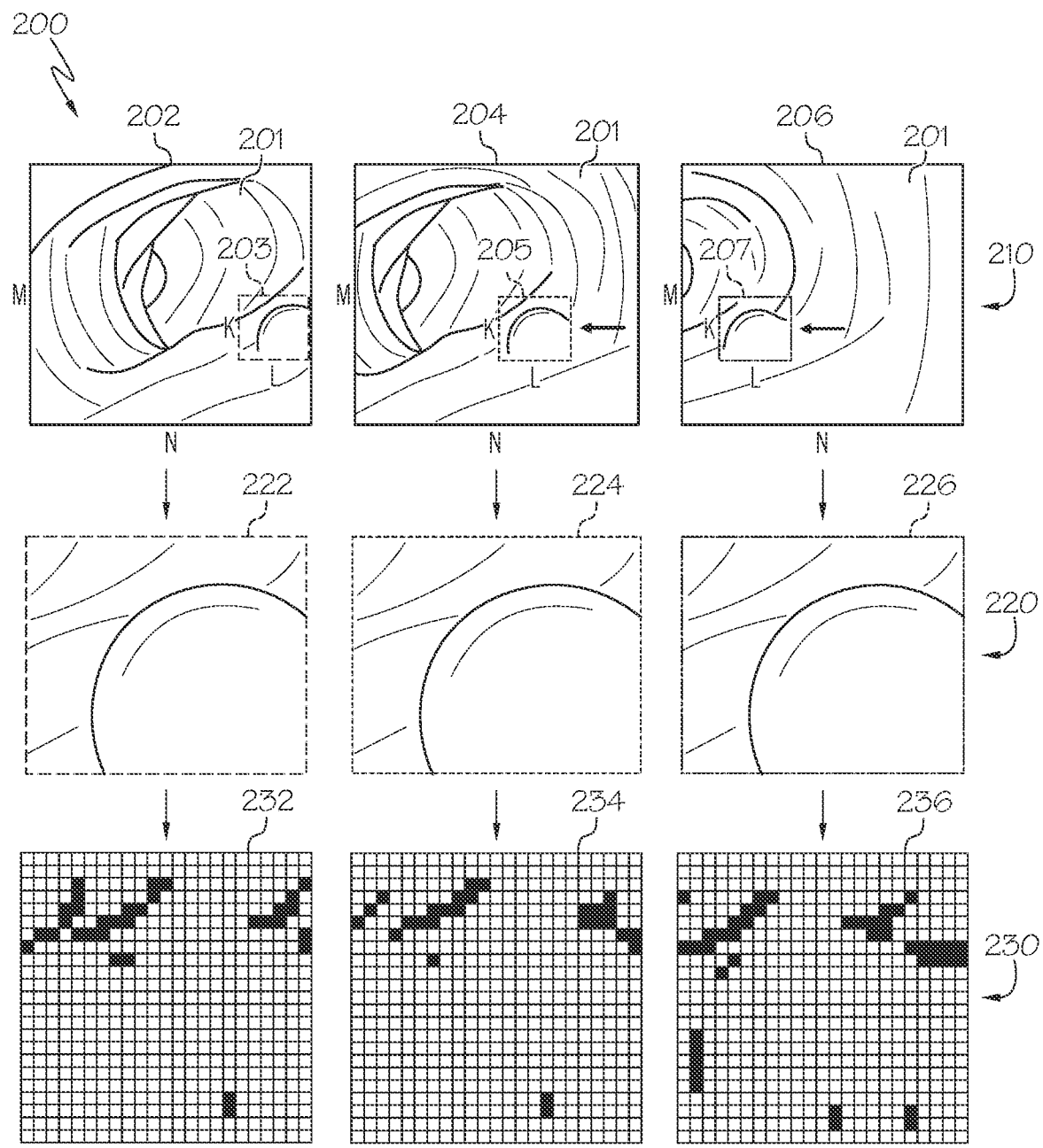
FIG. 2 illustrates an exemplary process of imaging a target site with the medical system of FIG. 1, according to aspects of this disclosure.

FIG. 2 shows a diagram for a multimodal image capturing and relative pixel block generating process 200 using the one or more image sensors 150 (hereinafter monochromatic image sensor 150) of the medical system 100 disclosed in accordance with FIG. 1. In comparison to image sensors with color filters, monochromatic image sensors can achieve higher quantum efficiency (e.g., sensitivity) and yield opportunities for better contrast definition as well as spectral flexibility when converting images captured by the monochromatic image sensor 150 into color images. Still referring to FIG. 2, at step 210, the monochromatic image sensor 150 may capture one or more images of a target site 201 (e.g., an esophagus, a stomach, a small intestine, other organs, tissue, polyp, etc.) of a subject (e.g., patient) that may be illuminated by the light source 130 (or the multicolor LED assembly) at the tip 122 of the shaft 120. For example, the target site 201 of the subject may be sequentially illuminated by the light source 130 (or the multicolor LED assembly) in different colors, for example, red, green, and blue (or cyan, magenta, or any other suitable colors for generating a color image). Accordingly, the monochromatic image sensor 150 may capture images at higher (e.g., three times or more) frame rates than a conventional color imager, in order to emulate the conventional color imager using a full spectrum illumination.

In one exemplary embodiment of FIG. 2, at step 210, the monochromatic image sensor 150 may initially capture at least three image frames of multimodal spectrum at the target site 201 when the light source 130 (or the multicolor LED assembly) may illuminate the target site 201 with, for example, a red light during a first frame 202, a blue light during a second frame 204, and a green light during a third frame 206. Each of the image frames captured during the three frames 202, 204, 206 may be identified by an M×N pixel block. In this instance, the image processing device 101 may adjust and adapt the three frames 202, 204, 206 of multimodal spectrum with any motion artifacts, in order to provide a crisp color image reproduction. That is, a target feature 203 defined by a K×L pixel block in the first frame 202 may be identified and tracked in the second frame 204 and the third frame 206 based on spatial displacements (e.g., motion) of the target feature 203 relative to a tip of the medical instrument 110, as illustrated by the relative positions of the target features 205 and 207 with respect to the target feature 203 position. Accordingly, each of the three frames 202, 204, and 206 that is illuminated with different colors (e.g., red, green, blue, etc.) may be identified with a matching K×L pixel block of target feature 203, 205, and 207, respectively.

In a given frame of M×N pixels (e.g., frame 202), identifying a matching block of pixel data of a predetermined size (e.g., K×L pixel block of the target feature 203) and the corresponding matching block of pixel data (e.g., K×L pixel block of the target feature 205 or 207) in the neighboring frames (e.g., frames 204 or 206) may be used for performing motion estimation and feature extraction, for example, tracking relevant key features moving in the given frame while the background remains the same. Conventional motion estimation techniques for target site imaging generally assume constant intensity from frame to frame. However, in the case of colorizing images captured by the monochromatic image sensor 150, each captured image frame (e.g., frames 202, 204, or 206) has a variable intensity due to the sequencing of multiple colors lights (e.g., red, green, blue, etc.). As such, applying the conventional motion estimation techniques of assuming constant intensity for images captured by the monochromatic image sensor 150 may not yield an accurate representation of the target feature movement/motion (e.g., spatial displacement of the target feature 203 as represented by the target features 205 and 207).

In one exemplary embodiment of this disclosure, each of the target features 203, 205, 207 may be identified in accordance with executable instructions or algorithms stored on the target extraction logic 105. For example, the target extraction logic 105 may include executable instructions and logarithmic, hierarchical, and/or exhaustive block matching algorithms. Further, the target extraction logic 105 may include executable instructions or algorithms for performing edge detection filtering on the target features 203, 205, and 207 to highlight key features in the K×L pixel blocks of the target features 203, 205, and 207. Accordingly, at step 220, the image processing device 101, in accordance with the executable instructions and algorithm stored on the target extraction logic 105, may extract K×L pixel block correlation features 222, 224, and 226 by performing edge detection filtering on the K×L pixel blocks of the target features 203, 205, and 207. In one embodiment, the extracted correlation feature 222 may include red color intensity data of the target feature 203, the correlation feature 224 may include blue color intensity data of the target feature 205, and the correlation feature 226 may include green color intensity data of the target feature 207.

Still referring to FIG. 2, at step 230, the processor 102 may generate, based on the executable instructions and algorithms in the intensity correlation logic 107, inter-block pixel to pixel intensity relationship maps 232, 234, and 236 for each of the edge converted K×L pixel block correlation features 222, 224, 226, respectively. For example, the intensity relationship map 232 may include pixel by pixel intensity data of the correlation feature 222 including red color intensity pixel data, the intensity relationship map 234 may include pixel by pixel intensity data of the correlation feature 224 including green color intensity pixel data, and the intensity relationship map 236 may include pixel by pixel intensity data of the correlation feature 226 including blue color intensity pixel data. Accordingly, the processor 102 may generate, in accordance with the executable instructions and algorithms of the intensity correlation logic 107, relative pixel blocks that may represent a best fit match for each of the target features 203, 205, and 207, by running the intensity relationship maps 232, 234, and 236 through a spatial correlation filter provided by the intensity correlation logic 107. The intensity pixel data of each pixel in the intensity relationship maps 232, 234, and 236 are represented in black and white in FIG. 2 for clarity. It is understood, however, that each pixel in the intensity relationship maps 232, 234, and 236 may be represented with various shades of gray, depending on the intensity detected by each pixel of the monochromatic image sensor 150.

In one embodiment, the intensity relationship maps 232, 234, and 236 may be substantially similar (e.g., slight variations due to the multimodal nature of the frames 202, 204, and 206). Further, each of the intensity relationship maps 232, 234, and 236 may provide a registration. That is, each relative pixel block generated based on the similarities in each of the intensity relationship maps 232, 234, and 236 may be utilized to align the estimated motion of a frame by cropping and overlaying the apriori frame's information with new changes in the subsequent frames. In one embodiment, the processor 102, may utilize the generated relative pixel blocks for colorizing the images of the target site 201 captured by the monochromatic image sensor 150.

In some embodiments, the processor 102 may speed up the relative pixel block generation process disclosed in accordance with FIG. 2 by applying a correlation matrix threshold scoring method. Performing edge filtering on the target features 203, 205, and 207 in accordance with the embodiments of this disclosure allows creating more efficient data sets in the form of intensity relationship maps 232, 234, 236 shown in FIG. 2. However, correlating two sets of data from these intensity relationship maps 232, 234, 236 may require searching for similar intensity distribution peaks. Due to the multimodal nature of the frames 202, 204, and 206, a perfect positive correlation (e.g., +1) may be difficult to achieve. Accordingly, creating a threshold scoring of, for example, a correlation score>+0.75 may insure a quicker matching of movement registration for the target features 203, 205, and 207, while maintaining a low video stream delay (e.g., less than 150 ms).

In one exemplary embodiment according to this disclosure, the processor 102 may utilize the following equation for generating relative pixel blocks:

Correlation Matrix Score>+0.75

For example, the processor 102 may generate or assign correlation scores for intensity distribution peaks for each of the intensity relationship maps 232, 234, and 236, and may then determine any correlation scores between two or more frames that are above +0.75 to be matching scores. The processor 102 may then generate the relative pixel blocks in accordance with the process 200 disclosed in FIG. 2. Further, the processor 102 may determine the best fit match of the target features 203, 205, and 207 in accordance with the intensity relationship maps 232, 234, 236 and the correlation matrix score equation.

In some embodiments, the processor 102 may perform, in accordance with the executable instructions or algorithms of the intensity normalization logic 107, relative intensity matching for generating relative pixel blocks in accordance with embodiments of this disclosure by normalizing the intensities of the different colors (e.g., red, green, blue, etc.)

detected in the image frames 202, 204, 206. The relative intensity of a target feature (e.g., target feature 203, 205, or 207) within an image frame (e.g., frames 202, 204, or 206) may depend on a specific color that may be used for illumination. Accordingly, in order to provide an estimate of the relative intensity between the different colors illuminated during the frames 202, 204, 206, each individual color channel's response to healthy tissue may be used. That is, while ignoring the effect of vascularity and other distinct features in the healthy tissue, the relative intensity between the color channels may be estimated by applying, for example, the following algorithm:

> Normalize a first color channel (e.g., red), to a value of 1

Using the same healthy tissue, the processor 102 may estimate the response of other color channels (e.g., green, blue, etc.) by comparing the other color channel responses to the first color (e.g., red) channel response. The processor 102 may then normalize the response of the other color channels to the same value of the first color channel response value. Once each color has been normalized based on the healthy tissue, the normalization factors (e.g., normalized color intensity values) may be used across varying anatomies to estimate the relative intensities of, for example, the red, green, and blue color channels. Accordingly, the relative intensities between the frames 202, 204, and 206 may be estimated more accurately for generating the relative pixel block in accordance with embodiments of this disclosure.

Figure 3:
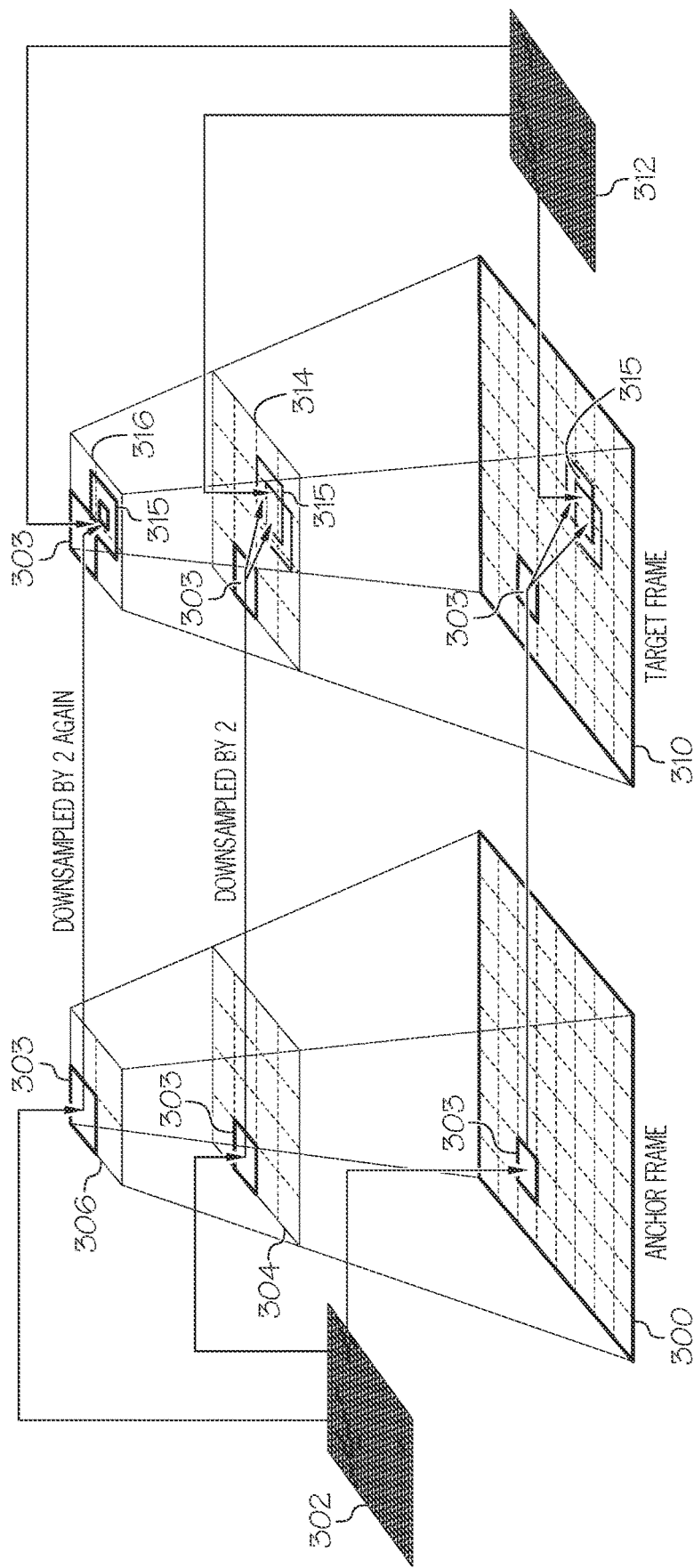
FIG. 3 illustrates an exemplary process of detecting motion in images captured using the medical system of FIG. 1, according to aspects of this disclosure.

FIG. 3 shows an exemplary image conversion process utilizing a hierarchical block matching algorithm to generate a relative pixel block in accordance with embodiments of this disclosure. In one embodiment, the monochromatic imaging sensor 150 may capture an anchor frame 300 and a target frame 310 of a target site of a subject (e.g., patient) in accordance with the process 200 disclosed in FIG. 2. In this embodiment, the processor 102 may utilize the executable instructions and algorithms stored in the memory (e.g., imaging logic 104, target extraction logic 105, intensity normalization logic 106, and/or intensity correlation logic 107) to perform the image conversion process described in accordance with FIG. 3. For example, the processor 101 of the image processing device 102 may determine or identify a target feature 303 at a first location of the anchor image frame 300 and at the corresponding first location of the target frame 310. Further, the processor 102 may determine a motion/spatial displacement of the target feature 303 identified in the anchor frame 300 by determining or identifying a displaced target feature 315 in accordance with the executable instructions or algorithms stored on the target extraction logic 105. Further, the processor 101 may generate inter-block pixel to pixel intensity relationship maps 302 and 312 in accordance with the process 200 disclosed in FIG. 2.

In one exemplary embodiment, the processor 102 may downsample the anchor frame 300 and the target frame 310, for example by two, into a first downsampled anchor frame 304 and a first downsampled target frame 314. The processor 101 may further downsample the first downsampled anchor frame 304 and the first downampled target frame 314 again, for example by two, to obtain a second downsampled anchor frame 306 and a second downsampled target frame 316. In this instance, the processor 102 may, for each of the anchor frames 300, 304, and 306, generate an inter-block pixel to pixel intensity relationship map 302 of the target feature 303 in accordance with the process 200 disclosed in FIG. 2. Further, in each of the target frames 310, 314, and 316, the processor 102 may identify the displaced target feature 315 and generate an inter-block pixel to pixel intensity relationship map 312 of the displaced target feature 315, in accordance with the process 200 disclosed in FIG. 2. Similar to FIG. 2, the intensity pixel data of each pixel in the intensity relationship maps 302 and 312 are represented in black and white in FIG. 3 for clarity. It is understood, however, that each pixel in the intensity relationship maps 302 and 312 may be represented with various shades of gray, depending on the intensity detected by each pixel of the monochromatic image sensor 150.

Still referring to FIG. 3, the processor 101 may generate relative pixel blocks based on the intensity relationship maps 302 and 312 at each hierarchical level (e.g., frames 300, 304, and 306 and frames 310, 314, and 316) in accordance with the process 200 disclosed in FIG. 2. In one embodiment, modified correlation matching scores may be used at each downsampled hierarchical level. Downsampling the anchor frame 300 and the target frame 310 reduces the search time within each of the frames of each hierarchical level by zooming into a region of interest for identifying the feature of interest (e.g., target features 303 and 315).

In one embodiment, a relative pixel block may be generated for each hierarchical level (e.g., frames 300, 304, and 306 and frames 310, 314, and 316). Different relative pixel block at each hierarchical level may be required to apply a hierarchical block matching algorithm described in accordance with FIG. 3. For example, each level of the highlighted block in the relative pixel blocks may vary from level to level based on the downsampling. That is, at one hierarchical level, a quadrant (e.g., frames 306 and 316) of an interested feature (e.g., 303 and 315) may be searched and located. At another hierarchical level a refining technique may be performed on a region of interest (e.g., frames 304 and 314), including an interested feature (e.g., 303 and 315). At a further hierarchical level, an actual image frame (e.g., frames 300 and 310) may be obtained based on the region of interest determined in the previous hierarchical levels. As such, fewer intensity blocks may need to be identified to determine the relative pixel block correlations at one hierarchical level (e.g., at frames 306 and 316) than at another hierarchical level (e.g., at frame 304 and 316). Further, a more detailed relative pixel block may be generated as the hierarchical level gets closer to an actual image (e.g., frame 300 and 310). Accordingly, a rapid determination of the interested features (e.g., 303, 315) may be made by downsampling twice (or more) and creating a different relative pixel block of the quadrant of the interested feature (303 and 315) at each hierarchical level (303, 304, and 306).

Figure 4A:
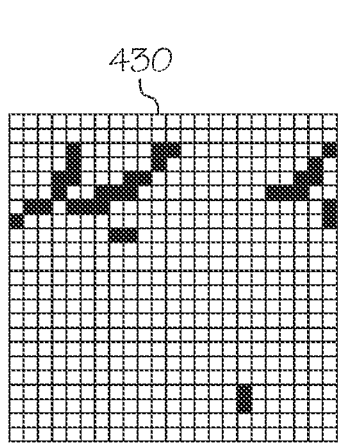
FIGS. 4A-4B illustrate another exemplary process of detecting motion in images captured using the medical system of FIG. 1, according to aspects of this disclosure.
Figure 4A:
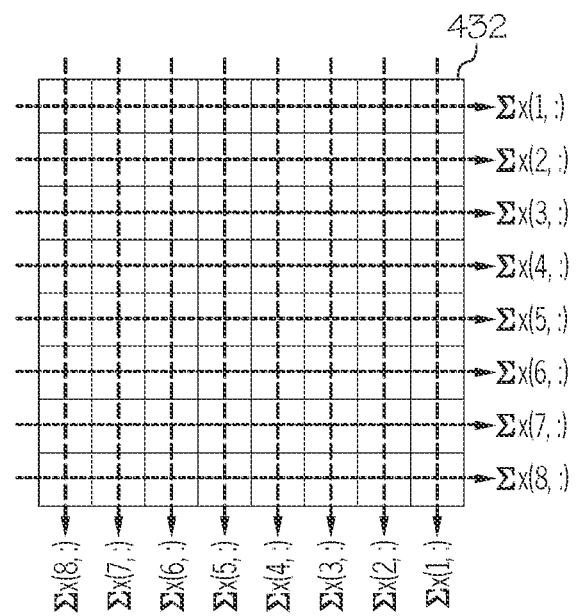
Figure 4B:
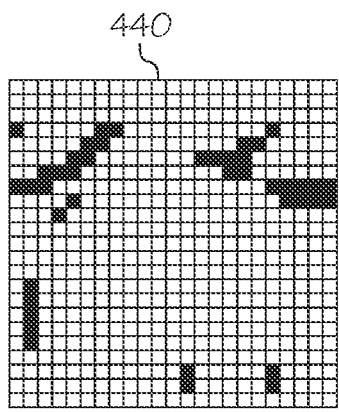
Figure 4B:
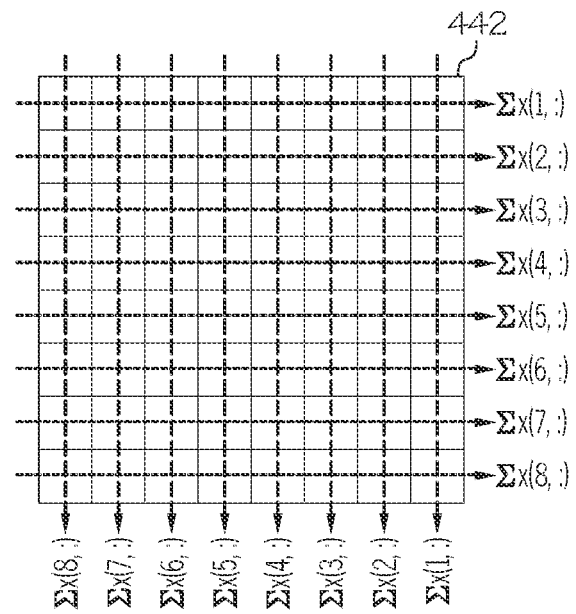

FIGS. 4A and 4B show an exemplary method of determining relative pixel blocks utilizing an indirect motion estimation through pixel projection. In this embodiment, intensity relationship maps of target feature images captured by a monochromatic image sensor 150 may be generated, in accordance with the process 200 in FIG. 2, prior to performing an indirect pixel projection method in accordance with the present disclosure. For example, as shown in FIGS. 4A-4B, the processor 102 may generate a first intensity relationship map 430 having intensity pixel values of a first color (e.g., blue) and a second intensity relationship map 440 having intensity pixel values of a second color (e.g., green). Thereafter, the processor 102 may generate two sets of pixel projection data in accordance with the first and second intensity relationship maps 430, 440. Additionally or alternatively to the process 200 in FIG. 2, the processor 102 may generate relative pixel blocks of the target feature by identifying peak intensity clusters of the two sets of pixel projection data in the columns and rows of a first pixel projection matrix 432 and a second pixel projection matrix 442 and determining the relative similarities between the identified peak intensity clusters. Similar to FIG. 2, the intensity pixel data of each pixel in the intensity relationship maps 430 and 440 are represented in black and white in FIG. 4 for clarity. It is understood, however, that each pixel in the intensity relationship maps 430 and 440 may be represented with various shades of gray, depending on the intensity detected by each pixel of the monochromatic image sensor 150.

In one exemplary embodiment, the rows and columns in the projection matrices 423, 442 may be summed to identify similar pixel densities between the matrices 423 and 442. For example, in the first pixel projection matrix 432 of FIG. 4A, summing up all of the dark pixels on the rows of the first intensity relationship map 430 may represent the locations of the pixel intensity distribution along the vertical axis. Further, summing up all the dark pixels shown in columns of the first intensity relationship map 430 may provide the location of the pixel intensity distribution along the horizontal axis. The similar process may be performed on the second pixel projection matrix 442 of FIG. 4B. The processor 102 may then identify the differences between the intensity pixel blocks (e.g., shifts in the pixel locations as shown in the intensity relationship maps 430 and 440) in FIG. 4A and FIG. 4B to generate the relative pixel block. Thus, the clusters of intensities in the intensity relationship maps 430 and 440 may be identified indirectly using the above-described summation technique to generate the relative pixel block.

Figure 5:
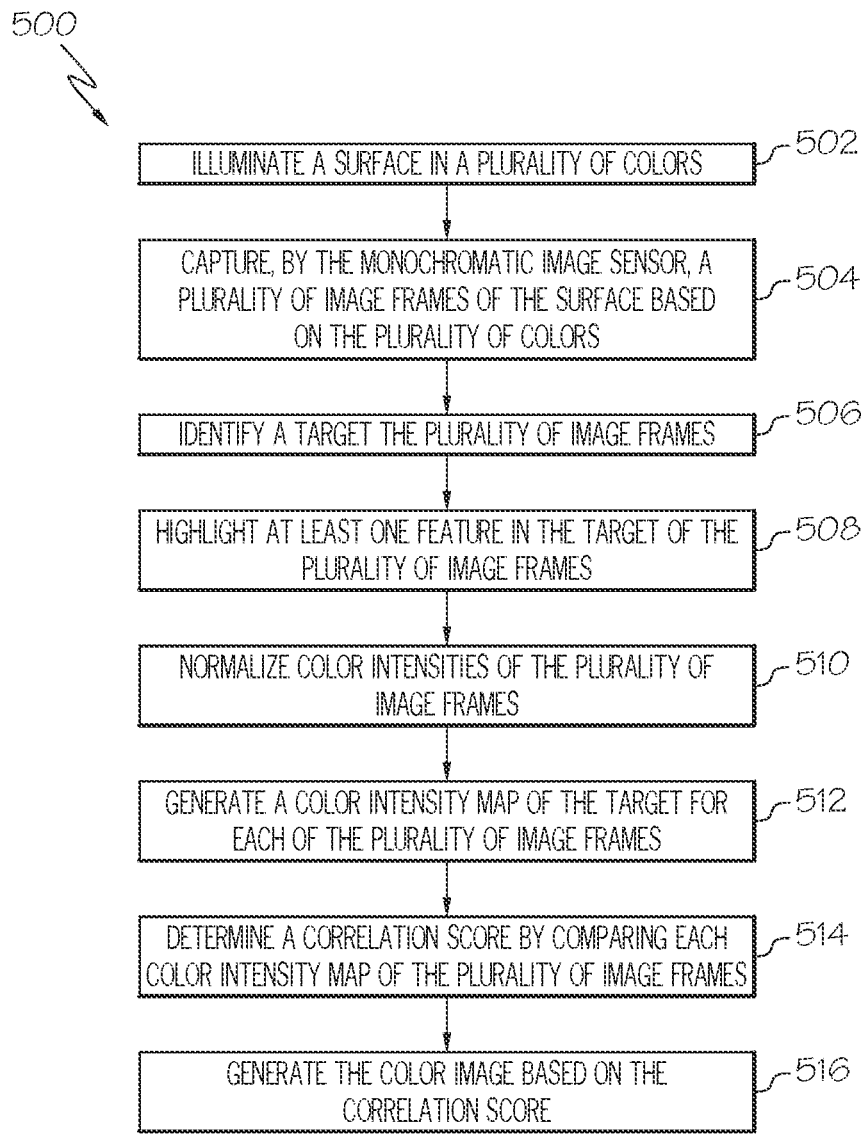
FIG. 5 illustrates a flow chart depicting an exemplary method of imaging a target site with the medical system of FIG. 1, according to aspects of this disclosure.

Generally, monochromatic image sensors only capture monochromatic images. As such, the images captured by the monochromatic image sensor 150 may emulate a color image sensor by colorizing the captured images based on variable pixel intensities detected during illumination of color lights (e.g., red, green, and red lights). Accordingly, FIG. 5 shows a flow diagram of an exemplary method 500 for generating a colorized image of a target site of a subject using the monochromatic image sensor 150. At step 502, the light source 130 of the medical system 100 may sequentially illuminate a surface (e.g., a target site of a patient) in a plurality of colors, one color at a time. In some embodiments, the plurality of colors may include at least one of red, green, or blue. In one embodiment, the surface may include a tissue of a gastrointestinal tract of a patient. At step 504, the monochromatic image sensor 150 may capture a plurality of image frames of the surface based on the plurality of colors. In one embodiment, the plurality of image frames may include at least a first image frame in a first color, a second image frame in a second color, and a third image frame in a third color. In one embodiment, the first color may be red, the second color may be green, and the third color may be blue. At step 506, the processor 102, in accordance with one or more of the imaging logic 104, the target extraction logic 105, the intensity normalization logic 106, and the intensity correlation logic 107 of the memory 103, may identify a target in the plurality of image frames. Further, a position of the target in a first frame of the plurality of frames may be different from a position of the target in a second frame of the plurality of frames. The processor 102 may utilize one or more logics (e.g., the imaging logic 104, the target extraction logic 105, the intensity normalization logic 106, and the intensity correlation logic 107) in the memory 103 to perform the steps described hereinafter. At step 508, the processor 102 may highlight at least one feature (e.g., target feature 203, 205, and/or 207) in the target of the plurality of image frames (e.g., frame 202, 204, and 206). In one embodiment, the processor 102 may apply an edge filter to extract at least one edge in the at least one feature.

At step 510, the processor 102 may normalize color intensities of the plurality of image frames. In one embodiment, in order to normalize the color intensities of the plurality of image frames, the light source 130 may illuminate the surface with a first color (e.g., red) of the plurality of colors. The processor 102 may then determine an intensity of the illuminated first color and assign a normalization value to the intensity of the first color. Thereafter, the light source 130 may illuminate the surface with a second color (e.g., green) of the plurality of colors. The processor 102 may then determine an intensity of the illuminated second color and generate a normalized intensity value of the second color based on the normalization value.

At step 512, the processor 102 may generate a color intensity map (e.g., intensity relationship maps 232, 234, or 236) of the target for each of the plurality of image frames (e.g., frames 202, 204, and 206). In one embodiment, the color intensity maps may include a plurality of pixels, and each of the plurality of pixels may include a color intensity value. Further, the target in each of the plurality of image frames may be compared based on the color intensity maps of the plurality of image frames. At step 514, the processor 102 may determine a correlation score by comparing each color intensity map of the plurality of image frames. In one embodiment, the processor 102 may determine peak intensity clusters in the color intensity maps and estimate motion of the target by comparing the peak intensity clusters in a first color intensity map and a second color intensity map.

At step 516, the processor 102 may generate the color image based on the correlation score. For example, the correlation score may be determined in less than 150 milliseconds. In one embodiment, the processor 102 may determine a matching pixel of the target between the first color intensity map and the second color intensity map when the correlation score is above a predetermined threshold value. Additionally or alternatively, the processor 102 may downsample the plurality of frames and determine the correlation score after downsampling the plurality of frames. In one embodiment, the processor 102 may downsample the plurality of frames by a factor of two at least twice.

Referring back to FIG. 1, which shows the display 109 of the medical system 100 communicatively coupled to the processor 102 of the image processing device 101, the processor 102 may be operable to transmit the colorized image generated in accordance with the methods 200 and 500 to the display 109 for viewing by a user of the medical system 100. In some examples, the medical system 100 may be configured and operable to continuously execute the methods 200 and 500 shown and described herein such that the display 109 may output a plurality of colorized images to provide a continuous (e.g., live, real-time, etc.) imaging of the one or more target objects.

Each of the aforementioned systems, devices, assemblies, and methods may be used to detect motion of a target feature in a target site of a subject and to generate colorized images of the target site. By providing a medical device including an image processing system, a user may enhance a visualization of one or more features and/or characteristics of a target site within a subject during a procedure by using monochromatic imaging sensors. The medical device may allow a user to accurately identify a location of a target site, thereby reducing overall procedure time, increasing efficiency of procedures, and avoiding unnecessary harm to a subject's body caused by inaccurately locating target objects in the target treatment site.

It will be apparent to those skilled in the art that various modifications and variations may be made in the disclosed devices and methods without departing from the scope of the disclosure. It should be appreciated that the disclosed devices may include various suitable computer systems and/or computing units incorporating a plurality of hardware components, such as, for example, a processor and non-transitory computer-readable medium, that allow the devices to perform one or more operations during a procedure in accordance with those described herein. Other aspects of the disclosure will be apparent to those skilled in the art from consideration of the specification and practice of the features disclosed herein. It is intended that the specification and examples be considered as exemplary only.

It should be appreciated that the image processing device 101 in FIG. 1 may be any computing device. The image processing device 101 also may include input and output ports to connect with input and output devices such as keyboards, mice, touchscreens, monitors, displays, etc. Of course, the various system functions may be implemented in a distributed fashion on a number of similar platforms, to distribute the processing load. Alternatively, the systems may be implemented by appropriate programming of one computer hardware platform.

In one embodiment, any of the disclosed systems, methods, and/or graphical user interfaces may be executed by or implemented by a computing system consistent with or similar to the descriptions herein. Although not required, aspects of the present disclosure are described in the context of computer-executable instructions, such as routines executed by a data processing device, e.g., a server computer, wireless device, and/or personal computer. Those skilled in the relevant art will appreciate that aspects of the present disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "computing device," and the like, are generally used interchangeably herein, and refer to any of the above devices and systems, as well as any data processor.

Aspects of the present disclosure may be embodied in a special purpose computer and/or data processor that is specifically programmed, configured, and/or constructed to perform one or more of the computer-executable instructions explained in detail herein. While aspects of the present disclosure, such as certain functions, are described as being performed exclusively on a single device, the present disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of the present disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of the present disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit switched, or other scheme).

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

It should be understood that one or more of the aspects of any of the medical devices described herein may be using in combination with any other medical device known in the art, such as medical imaging systems or other scopes such as colonoscopes, bronchoscopes, ureteroscopes, duodenoscopes, etc., or other types of imagers.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A method of generating a color image using a monochromatic image sensor, the method comprising:

sequentially illuminating a surface in a plurality of colors, one color at a time;
capturing, by the monochromatic image sensor, a plurality of image frames of the surface based on the plurality of colors;
identifying a target in the plurality of image frames;
highlighting at least one feature in the target of the plurality of image frames;
normalizing color intensities of the plurality of image frames;
generating a color intensity map of the target for each of the plurality of image frames;
determining a correlation score by comparing each color intensity map of the plurality of image frames; and
generating the color image based on the correlation score.

2. The method of claim 1, wherein the plurality of image frames includes at least a first image frame in a first color and a second image frame in a second color.

3. The method of claim 1, wherein the normalizing the color intensities of the plurality of image frames comprises:
illuminating the surface with a first color of the plurality of colors;
determining an intensity of the illuminated first color; and
assigning a normalization value to the intensity of the first color.

4. The method of claim 3, wherein the normalizing the color intensities of the plurality of image frames further comprises:
illuminating the surface with a second color of the plurality of colors;
determining an intensity of the illuminated second color; and
generating a normalized intensity value of the second color based on the normalization value.

5. The method of claim 1, wherein the plurality of colors comprises at least one of red, green, or blue.

6. The method of claim 1, wherein the highlighting the at least one feature in the target comprises:
applying an edge filter to extract at least one edge in the at least one feature.

7. The method of claim 1, wherein the color intensity map of the target for each of the plurality of image frames comprises a plurality of pixels; and
each of the plurality of pixels has a color intensity value.

8. The method of claim 1, wherein the target in each of the plurality of image frames is compared based on the color intensity map of the target for each of the plurality of image frames.

9. The method of claim 1, further comprising:
determining a matching pixel of the target between a first color intensity map and a second color intensity map when the correlation score is above a predetermined threshold value.

10. The method of claim 1, further comprising:
downsampling the plurality of image frames; and
determining the correlation score after downsampling the plurality of image frames.

11. The method of claim 10, further comprising downsampling the plurality of image frames by a factor of two at least twice.

12. The method of claim 1, further comprising:
determining peak intensity clusters in the color intensity map of the target for each of the plurality of image frames; and
estimating motion of the target by comparing the peak intensity clusters in a first color intensity map and a second color intensity map.

13. The method of claim 1, wherein a position of the target in a first frame of the plurality of image frames is different from a position of the target in a second frame of the plurality of image frames.

14. The method of claim 1, wherein the correlation score is determined in less than 150 milliseconds.

15. The method of claim 1, wherein the surface comprises a tissue of a gastrointestinal tract.

16. A medical device, comprising:
a shaft;
a monochromatic image sensor coupled to a distal end of the shaft;
at least one illumination device coupled to the distal end of the shaft, the at least one illumination device being configured to emit a plurality of colors, one color at a time;
one or more computer readable media storing instructions for performing an image processing using the monochromatic image sensor; and
one or more processors configured to execute the instructions to perform the image processing comprising:
sequentially illuminating a surface in a plurality of colors;
capturing, by the monochromatic image sensor, a plurality of image frames of the surface based on the plurality of colors;
identifying a target in the plurality of image frames;
highlighting at least one feature in the target of the plurality of image frames;
normalizing color intensities of the plurality of image frames;
generating a color intensity map of the target for each of the plurality of image frames;
determining a correlation score by comparing each color intensity map of the plurality of image frames; and
generating a color image based on the correlation score.

17. The medical device of claim 16, wherein the at least one illumination device is configured to selectively emit at least one of red, blue, and green colors.

18. The medical device of claim 16, wherein the normalizing the color intensities of the plurality of image frames comprises:
illuminating the surface with a first color of the plurality of colors;
determining an intensity of the illuminated first color; and
assigning a normalization value to the intensity of the first color.

19. The medical device of claim 18, wherein the normalizing the color intensities of the plurality of image frames further comprises:
illuminating the surface with a second color of the plurality of colors;
determining an intensity of the illuminated second color; and
generating a normalized intensity value of the second color based on the normalization value.

20. A non-transitory computer-readable medium storing instructions for performing image processing using a monochromatic image sensor, the instructions, when executed by one or more processors, causing the one or more processors to perform operations comprising:
sequentially illuminating a surface in a plurality of colors, one color at a time;
capturing, by the monochromatic image sensor, a plurality of image frames of the surface based on the plurality of colors;
identifying a target in the plurality of image frames;

highlighting at least one feature in the target of the plurality of image frames;
normalizing color intensities of the plurality of image frames;
generating a color intensity map of the target for each of the plurality of image frames;
determining a correlation score by comparing each color intensity map of the plurality of image frames; and
generating a color image based on the correlation score.

* * * * *